(12) United States Patent
Sista

(10) Patent No.: US 10,487,077 B1
(45) Date of Patent: Nov. 26, 2019

(54) BIS(BENZOXAZINYL)PHTHALIMIDINE AND ASSOCIATED CURABLE COMPOSITION AND COMPOSITE

(71) Applicant: SABIC Global Technologies B.V., Bergen op Zoom (NL)

(72) Inventor: Prakash Sista, Evansville, IN (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/376,289

(22) Filed: Apr. 5, 2019

(30) Foreign Application Priority Data

Jun. 14, 2018 (EP) ...................................... 18177776

(51) Int. Cl.
*C07D 413/14* (2006.01)
*C07D 405/14* (2006.01)

(52) U.S. Cl.
CPC ......... *C07D 413/14* (2013.01); *C07D 405/14* (2013.01)

(58) Field of Classification Search
CPC ............................ C07D 413/14; C07D 405/14
USPC .......................................................... 544/73
See application file for complete search history.

(56) References Cited

U.S. PATENT DOCUMENTS

| | | |
|---|---|---|
| 5,344,910 A | 9/1994 | Sybert |
| 5,455,310 A | 10/1995 | Hoover et al. |
| 7,135,577 B2 | 11/2006 | Rai et al. |
| 7,277,230 B2 | 10/2007 | Srinivasan et al. |
| 7,329,720 B2 | 2/2008 | Ganesan et al. |
| 7,348,439 B2 | 3/2008 | Ganesan et al. |
| 7,354,986 B2 | 4/2008 | Mahood et al. |
| 7,408,016 B2 | 8/2008 | Chatterjee et al. |
| 7,470,796 B2 | 12/2008 | Rai et al. |
| 7,491,788 B1 | 2/2009 | Leenders et al. |
| 7,495,066 B2 | 2/2009 | Balikrishnan et al. |
| 7,514,524 B2 | 4/2009 | Basale et al. |
| 7,563,817 B2 | 7/2009 | Ganesan et al. |
| 7,592,464 B2 | 9/2009 | Basale et al. |
| 7,642,315 B2 | 1/2010 | Davis et al. |
| 7,649,073 B2 | 1/2010 | Davis et al. |
| 7,790,832 B2 | 9/2010 | Ganesan et al. |
| 7,838,689 B2 | 11/2010 | Bhotla et al. |
| 7,842,379 B2 | 11/2010 | Thiagarajan et al. |
| 7,868,190 B2 | 1/2011 | Bhotla et al. |
| 7,884,220 B2 | 2/2011 | Xu et al. |
| 7,915,430 B2 | 3/2011 | Bhotla et al. |
| 7,935,777 B2 | 5/2011 | De Kraker et al. |
| 7,999,037 B2 | 8/2011 | Jansen et al. |
| 8,022,166 B2 | 9/2011 | De Kraker et al. |
| 8,064,140 B2 | 11/2011 | Hoeks et al. |
| 8,106,144 B2 | 1/2012 | Ooms et al. |
| 8,247,523 B2 | 8/2012 | Bhotla et al. |
| 8,487,065 B2 | 7/2013 | Mahood et al. |
| 8,525,191 B2 | 9/2013 | Zhou et al. |
| 8,669,315 B2 | 3/2014 | Gallucci et al. |
| 8,779,040 B2 | 7/2014 | Van Der Weele et al. |
| 8,779,162 B2 | 7/2014 | Ikeno et al. |
| 9,051,463 B2 | 6/2015 | Uno et al. |
| 9,062,196 B2 | 6/2015 | Chatterjee et al. |
| 9,115,283 B2 | 8/2015 | Rosenquist et al. |
| 9,127,119 B2 | 9/2015 | Rai et al. |
| 9,127,155 B2 | 9/2015 | Subramanian et al. |
| 9,266,541 B2 | 2/2016 | Van Der Mee et al. |
| 9,328,240 B2 | 5/2016 | Van Der Mee et al. |
| 9,441,106 B2 | 9/2016 | Zhou et al. |
| 9,490,405 B2 | 11/2016 | Evans et al. |
| 9,546,269 B2 | 1/2017 | Vollenberg et al. |
| 9,553,244 B2 | 1/2017 | Morizur et al. |
| 9,580,595 B2 | 2/2017 | Morizur et al. |
| 2008/0161507 A1 | 7/2008 | Chakravarti et al. |
| 2011/0152453 A1 | 6/2011 | Tietze et al. |
| 2015/0210806 A1 | 7/2015 | Peters |
| 2016/0168323 A1 | 6/2016 | Hollar, Jr. et al. |
| 2016/0177029 A1 | 6/2016 | Hollar, Jr. et al. |

(Continued)

FOREIGN PATENT DOCUMENTS

| | | |
|---|---|---|
| CN | 106478488 A | 3/2017 |
| CN | 107004806 A | 8/2017 |

(Continued)

OTHER PUBLICATIONS

European Search Report dated Jul. 27, 2018; EP Application No. 18177776A; EP Filing Date Jun. 14, 2018 (18 pages).
Yang et al., "Copolymers of Phenolphthalein-aniline-based Benzoxazine and Biphenyl Epoxy: Curing Behavior and Thermal and Mechanical Properties" J Polym Res (2012) vol. 19 (9 pages).

(Continued)

*Primary Examiner* — Kahsay Habte
(74) *Attorney, Agent, or Firm* — Cantor Colburn LLP

(57) ABSTRACT

A bis(benzoxazinyl)phthalimidine has the structure

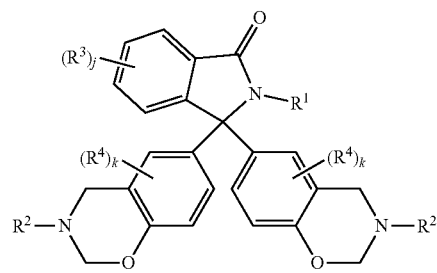

wherein $R^1$, $R^2$, $R^3$, $R^4$, j, and k are defined herein. The bis(benzoxazinyl)phthalimidine is useful as a component of a curable composition. It exhibits a high melting temperature and a high exotherm onset temperature. Also described is a composite that includes a reinforcing filler and the curing product of the bis(benzoxazinyl)phthalimidine.

14 Claims, 1 Drawing Sheet

(56) References Cited

U.S. PATENT DOCUMENTS

| | | |
|---|---|---|
| 2016/0180985 A1 | 6/2016 | Silvi et al. |
| 2016/0237210 A1 | 8/2016 | Mahood et al. |
| 2016/0340307 A1 | 11/2016 | Bhotla et al. |
| 2017/0002236 A1 | 1/2017 | Papenbroock et al. |
| 2017/0022359 A1 | 1/2017 | Farrell et al. |
| 2017/0022360 A1 | 1/2017 | Farrell et al. |
| 2017/0022361 A1 | 1/2017 | Grieshaber et al. |
| 2017/0022362 A1 | 1/2017 | Grieshaber et al. |
| 2017/0029562 A1 | 2/2017 | Pillai et al. |
| 2017/0029618 A1 | 2/2017 | Grieshaber et al. |
| 2017/0037243 A1 | 2/2017 | Grieshaber et al. |
| 2017/0037245 A1 | 2/2017 | Van De Wetering |
| 2018/0215915 A1 | 8/2018 | Seidel et al. |

FOREIGN PATENT DOCUMENTS

| | | |
|---|---|---|
| EP | 1797081 B1 | 11/2008 |
| EP | 3406648 A1 | 11/2018 |
| GB | 1158606 | 2/1967 |
| GB | 1282529 | 7/1972 |
| JP | 2283726 A | 11/1990 |
| JP | 2648359 B2 | 8/1997 |
| JP | 02820277 B2 | 11/1998 |
| JP | 3297469 B2 | 7/2002 |
| JP | 4316959 B2 | 8/2009 |
| JP | 5687120 B2 | 3/2015 |
| JP | 5805982 B2 | 11/2015 |
| JP | 2016044229 A | 4/2016 |
| JP | 6061234 B1 | 1/2017 |
| JP | 2017071706 A | 4/2017 |
| KR | 1020170001987 | 1/2017 |
| KR | 1020170089913 | 8/2017 |
| KR | 1020170091675 | 8/2017 |
| WO | 2013148408 A1 | 10/2013 |
| WO | 2013183736 A1 | 12/2013 |
| WO | 2014175346 A1 | 10/2014 |
| WO | 2015037584 A1 | 3/2015 |
| WO | 2015064607 A1 | 5/2015 |
| WO | 2015195527 A1 | 12/2015 |
| WO | 2016011332 A1 | 1/2016 |
| WO | 2016011334 A1 | 1/2016 |
| WO | 2016031643 A1 | 3/2016 |
| WO | 2016063154 A1 | 4/2016 |
| WO | 2016176194 A1 | 11/2016 |
| WO | 2017003809 A1 | 1/2017 |
| WO | 2017033146 A1 | 3/2017 |
| WO | 2017072676 A1 | 5/2017 |
| WO | 2017188448 A1 | 3/2019 |

OTHER PUBLICATIONS

Yang et al., "Synthesis and Curing Behavior of a Benzoxazine Based on Phenolphthalein and its High Performance Polymer" J Polym Res vol. 18 (2011) pp. 1725-1733.

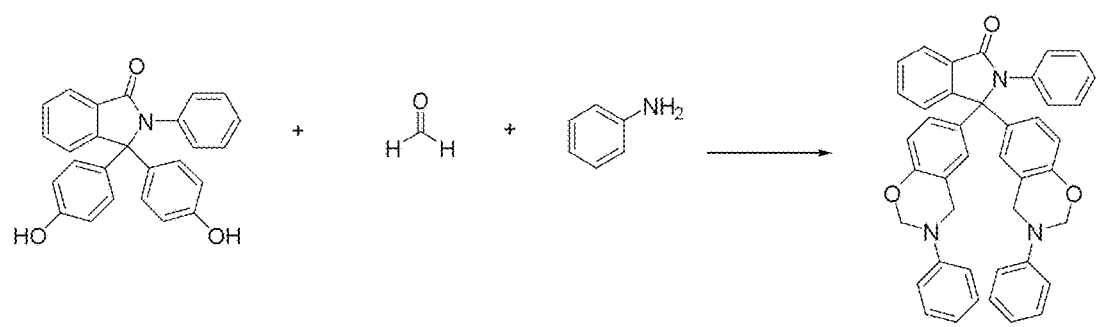

BIS(BENZOXAZINYL)PHTHALIMIDINE AND ASSOCIATED CURABLE COMPOSITION AND COMPOSITE

CROSS-REFERENCE TO RELATED APPLICATIONS

This application claims priority from European Patent Application No. 18177776.4 filed on Jun. 14, 2018, which is incorporated by reference herein in its entirety.

BACKGROUND OF THE INVENTION

Benzoxazines are a class of thermoset materials that are useful in the fabrication of electronic devices and other composites. Benzoxazines can undergo thermal curing with or without a curing catalyst to form polybenzoxazines. Relative to epoxy thermosets, benzoxazines typically cure at lower temperatures and do not require curing catalysts or hardening agents. Cured thermosets derived from benzoxazines also absorb much less moisture than those derived from epoxies. Benzoxazines also demonstrate near-zero shrinkage during curing (which is a significant improvement from epoxy resins), and no volatiles are released during curing reactions. Polybenzoxazines offer a low melt viscosity, high glass transition temperature, high thermal stability, good mechanical strength, low dielectric constant and good resistance to burning. In addition, the cure exotherms for benzoxazines are much lower than those of epoxies, thereby allowing fabrication of thicker sections, longer injection times, and larger parts.

Compounds containing two benzoxazine groups (i.e., bis(benzoxazinyl) compounds) are known. See, for example, U.S. Patent Application No. US 2011/0152453 A1 of Tietze et al., which describes bis(benzoxazinyl) derivatives of phenolphthalein. However, there is a desire for bis(benzoxazinyl) compounds exhibiting higher melting temperatures and higher exotherm onset temperatures.

BRIEF SUMMARY OF EMBODIMENTS OF THE INVENTION

One embodiment is a bis(benzoxazinyl)phthalimidine having the structure

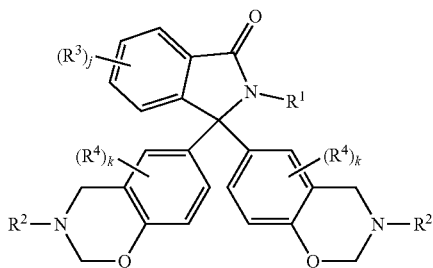

wherein R' is hydrogen, $C_1$-$C_6$ alkyl, phenyl, or phenyl substituted with up to five substituents independently selected from halogen and $C_1$-$C_6$ alkyl; each occurrence of $R^2$ is independently selected from the group consisting of unsubstituted or substituted $C_1$-$C_{30}$ hydrocarbyl; each occurrence of $R^3$ is independently $C_1$-$C_6$ alkyl; j is 0, 1, 2, 3, or 4; each occurrence of $R^4$ is independently selected from the group consisting of $C_1$-$C_{12}$ alkyl, $C_2$-$C_{12}$ alkenyl, $C_1$-$C_{12}$ alkoxyl; and each occurrence of k is independently 0, 1, 2, or 3.

Another embodiment is a curable composition comprising the bis(benzoxazinyl)phthalimidine in any of its variations.

Another embodiment is a composite comprising a reinforcing filler and a curing product of the bis(benzoxazinyl)phthalimidine in any of its variations.

These and other embodiments are described in detail below.

BRIEF DESCRIPTION OF THE DRAWING

The FIGURE is a chemical scheme for the synthesis of 2-phenyl-3,3-bis(3-phenyl-3,4-dihydro-2H-benzo [e][1,3] oxazin-6-yl)isoindolin-1-one.

DETAILED DESCRIPTION OF THE INVENTION

The present inventors have determined that a bis(benzoxazinyl)phthalimidine compound exhibits a higher melting temperature and higher exotherm onset temperature than a corresponding bis(benzoxazinyl)phenophthalein compound.

One embodiment is a bis(benzoxazinyl)phthalimidine having the structure

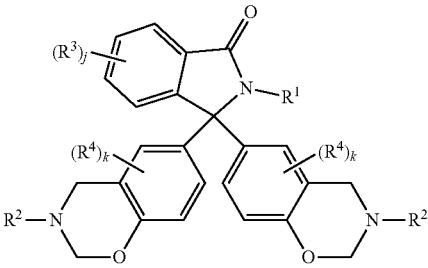

wherein $R^1$ is hydrogen, $C_1$-$C_6$ alkyl, phenyl, or phenyl substituted with up to five substituents independently selected from halogen and $C_1$-$C_6$ alkyl; each occurrence of $R^2$ is independently selected from the group consisting of unsubstituted or substituted $C_1$-$C_{30}$ hydrocarbyl; each occurrence of $R^3$ is independently $C_1$-$C_6$ alkyl; j is 0, 1, 2, 3, or 4; each occurrence of $R^4$ is independently selected from the group consisting of $C_1$-$C_{12}$ alkyl, $C_2$-$C_{12}$ alkenyl, and $C_1$-$C_{12}$ alkoxyl; and each occurrence of k is independently 0, 1, 2, or 3.

As used herein, the term "hydrocarbyl", whether used by itself, or as a prefix, suffix, or fragment of another term, refers to a residue that contains only carbon and hydrogen unless it is specifically identified as "substituted hydrocarbyl". The hydrocarbyl residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. When the hydrocarbyl residue is described as substituted, it can contain heteroatoms in addition to carbon and hydrogen.

As used herein, the term "alkyl" includes linear, branched, cyclic, and polycyclic alkyl groups, as well as alkyl groups having a combination of at least two types of linear, branched, cyclic, and polycyclic alkyl fragments.

As used herein, the term "halogen" means fluoro, chloro, bromo, or iodo.

When not otherwise expressly defined, the term "substituted" means including at least one substituent such as a halogen, hydroxyl, amino, thiol, carboxyl, carboxylate, amide, cyano, sulfide, disulfide, nitro, $C_1$-$C_{18}$ alkyl, $C_1$-$C_{18}$ alkoxyl, $C_6$-$C_{18}$ aryl, $C_6$-$C_{18}$ aryloxyl, $C_7$-$C_{18}$ alkylaryl, or $C_7$-$C_{18}$ alkylaryloxyl. "Substituted" further means including at least one heteroatom within the carbon framework, as contrasted with pendant to the carbon framework. For example, substituted aryl includes pyridyl.

In some embodiments of the bis(benzoxazinyl)phthalimidine, $R^1$ is phenyl, or phenyl substituted with 1, 2, 3, 4, or 5 substituents independently selected from halogen and $C_1$-$C_6$ alkyl. In some embodiments, $R^1$ is phenyl.

In some embodiments of the bis(benzoxazinyl)phthalimidine, each occurrence of $R^2$ is independently selected from the group consisting of $C_1$-$C_{12}$ alkyl (including, for example, cyclopropyl, cyclobutyl, cyclopentyl, cyclohexyl, cycloheptyl, and cyclooctyl), anthracenyl, biphenyl, cyclohexenyl, cyclopentenyl, indanyl, naphthyl, and phenyl. In some embodiments, each occurrence of $R^2$ is $C_1$-$C_{12}$ alkyl or phenyl. In some embodiments, each occurrence of $R^2$ is phenyl. In some embodiments, $R^1$ is phenyl, and each occurrence of $R^2$ is phenyl.

In some embodiments, j is 0. In some embodiments, each occurrence of k is 0. In some embodiments, j is 0, and each occurrence of k is 0.

A representative synthesis of a bis(benzoxazinyl)phthalimidine is provided in the working examples below. In general, the bis(benzoxazinyl)phthalimidine can be synthesized by reacting a 3,3-bis(4-hydroxyphenyl)phthalimidine substituted in the 2-position with the desired $R^1$ group with at least two equivalents of paraformaldehyde or other formaldehyde equivalent, and with at least two equivalents of an amine substituted with the desired $R^2$ group. The resulting product bis(benzoxazinyl)phthalimidine can be purified by conventional methods, including chromatography, precipitation, recrystallization, and combinations thereof.

Another embodiment is a curable composition comprising the bis(benzoxazinyl)phthalimidine in any of its above-described variations. The bis(benzoxazinyl)phthalimidine can be cured in the absence of any curing catalyst or curing agent. So, it is possible for the curable composition to consist of the bis(benzoxazinyl)phthalimidine.

In other embodiments, the curable composition comprises, in addition to the bis(benzoxazinyl)phthalimidine, an epoxy compound. The bis(benzoxazinyl)phthalimidine and the epoxy compound can be co-cured without the need for any of the curing agents or curing catalysts typically required by epoxy compounds.

Epoxy compounds include, for example, aliphatic epoxy resins, cycloaliphatic epoxy resins, aromatic epoxy resins (including bisphenol-A epoxy resins, bisphenol-F epoxy resins, phenol novolac epoxy resins, cresol-novolac epoxy resins, biphenyl epoxy resins, triglycidyl p-aminophenol, tetraglycidyl diamino diphenyl methane, naphthalene epoxy resins, 2-glycidylphenylglycidyl ether, 4-glycidylphenylglycidyl ether, 2-phenyl-3,3-bis(4-glycidyloxyphenyl)phthalimidine, and multi-aromatic resin (MAR-type) epoxy resins), dicyclopentadiene-type (DCPD-type) epoxy resins, and combinations thereof.

In some embodiments, the epoxy compound is selected from the group consisting of bisphenol-A epoxy resins, bisphenol-F epoxy resins, neopentylglycol epoxy resins, 3,4-epoxycyclohexylmethyl-3,4-epoxycyclohexane carboxylate, N,N-diglycidyl-4-glycidyloxyaniline, N,N,N',N'-tetraglycidyl-4,4'-diaminodiphenylmethane, 2-phenyl-3,3-bis(4-glycidyloxyphenyl)phthalimidine, and combinations thereof.

In some embodiments, the curable composition further comprises, in addition to the bis(benzoxazinyl)phthalimidine, a diglycidyl ether compound having the structure

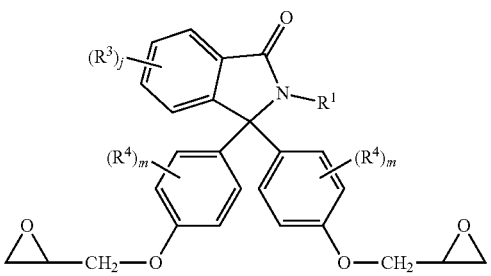

wherein $R^1$ is hydrogen, $C_1$-$C_6$ alkyl, phenyl, or phenyl substituted with up to five substituents independently selected from halogen and $C_1$-$C_6$ alkyl; each occurrence of $R^3$ is independently $C_1$-$C_6$ alkyl; j is 0, 1, 2, 3, or 4; each occurrence of $R^4$ is independently selected from the group consisting of $C_1$-$C_{12}$ alkyl, $C_2$-$C_{12}$ alkenyl, and $C_1$-$C_{12}$ alkoxyl; and each occurrence of m is independently 0, 1, 2, 3, or 4.

In some embodiments of the diglycidyl ether compound, R' is phenyl, or phenyl substituted with 1, 2, 3, 4, or 5 substituents independently selected from halogen and $C_1$-$C_6$ alkyl.

In some embodiments, $R^1$ is phenyl.

In some embodiments of the diglycidyl ether compound, j is 0. In some embodiments of the diglycidyl ether compound, each occurrence of k is 0. In some embodiments of the diglycidyl ether compound, j is 0, and each occurrence of k is 0.

In a very specific embodiment of the curable composition, the bis(benzoxazinyl)phthalimidine has the structure

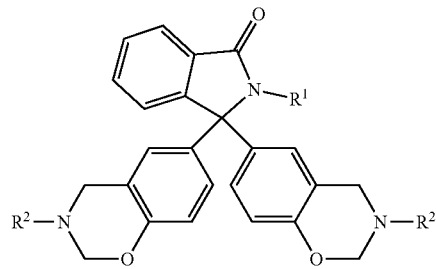

wherein $R^1$ is phenyl, and each occurrence of $R^2$ is $C_1$-$C_{12}$ alkyl or phenyl. In some embodiments, each occurrence of $R^2$ is phenyl.

The curable composition comprises the bis(benzoxazinyl)phthalimidine in an amount of 10 to 100 weight percent, based on the total weight of the curable composition. Within this range, the amount of bis(benzoxazinyl)phthalimidine can be 25 to 100 weight percent, or 50 to 100 weight percent, or 75 to 100 weight percent, or 90 to 100 weight percent, or 95 to 100 weight percent.

When the curable composition comprises the bis(benzoxazinyl)phthalimidine and the diglycidyl ether compound, the composition can comprise 10 to 90 weight percent of the bis(benzoxazinyl)phthalimidine and 10 to 90 weight percent of the diglycidyl ether compound, based on the total weight of the curable composition. Within these ranges, the curable composition can comprise 25 to 75 weight percent of the bis(benzoxazinyl)phthalimidine and 25 to 75 weight percent of the diglycidyl ether compound, or 40 to 60 weight percent of the bis(benzoxazinyl)phthalimidine and 40 to 60 weight percent of the diglycidyl ether compound.

The curable composition can, optionally, further comprise one or more thermoset additives. Such additive include, for example, flame retardants, lubricants, mold release agents, antioxidants, thermal stabilizers, ultraviolet stabilizers, colorants (including pigments and dyes), anti-static agents, and combinations thereof. When present, such additives can be used in a total amount of 1 part per million by weight to 20 weight percent, based on the total weight of the composition. Within this range, the total amount of colorants can be 0.1 to 10 weight percent, or 0.2 to 5 weight percent.

The curable composition can, optionally, further include a filler. Fillers include, for example, silica, boron nitride, boron-silicate, alumina, aluminum diboride, magnesium oxide, wollastonite, calcium sulfate, calcium carbonate, talc, basalt, glass fibers, glass flakes, glass spheres, kaolin, mica, feldspar, nepheline syenite, flue dust, cenospheres, fillite, natural silica sand, quartz, quartzite, perlite, tripoli, diatomaceous earth, silicon carbide, molybdenum sulfide, zinc sulfide, aluminum silicate (mullite), calcium silicate, zirconium silicate, barium titanate, barium ferrite, barium sulfate, particulate and fibrous aluminum, particulate and fibrous bronze, particulate and fibrous zinc, particulate and fibrous copper, particulate and fibrous nickel, particulate and fibrous steel, particulate and fibrous conductive carbon, polyester fibers, aromatic polyamide fibers, polyimide fibers, poly(phenylene sulfide) fibers, polyether ether ketone fibers, and combinations thereof.

In some embodiments, the filler is a reinforcing filler. Reinforcing fillers include, for example, metal fibers, metallized inorganic fibers, metallized synthetic fibers, glass fibers, graphite fibers, carbon fibers, ceramic fibers, mineral fibers, basalt fibers, polymer fibers having a melting or glass transition temperature at least 100° C. higher than decomposition onset temperature of the bis(benzoxazinyl)phthalimidine (including aramid fibers), and combinations thereof. It will be understood that the reinforcing fillers can be in the form of woven fabrics (including plain weave fabrics, satin weave fabrics, and non-crimp fabrics), non-woven fabrics, unidirectional fibers, braided fibers, fiber tow, and fiber ropes.

When present, the fillers can be used in an amount of 0.5 to 1000 weight parts, based on 100 parts by weight of the bis(benzoxazinyl)phthalimidine. Within this range, the filler amount can be 10 to 500 weight parts, or 20 to 400 weight parts.

Another embodiment is a composite comprising a reinforcing filler and the curing product of the bis(benzoxazinyl)phthalimidine in any of its above-described variations.

Reinforcing fillers are describe above in the context of the curable composition. In some embodiments, the reinforcing filler is selected from the group consisting of glass fiber, carbon fiber, and combinations thereof.

In a very specific embodiment of the composite, the bis(benzoxazinyl)phthalimidine has the structure

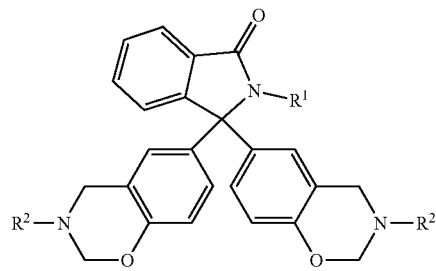

wherein $R^1$ is phenyl, and each occurrence of $R^2$ is phenyl.

In addition to the reinforcing filler and a curing product of the bis(benzoxazinyl)phthalimidine, the composite can, optionally, further comprise a curing product of an epoxy compound. Epoxy compounds are describe above in the context of the curable composition.

The composite comprises the reinforcing filler in an amount of 0.5 to 1000 weight parts, based on 100 parts by weight of a curing product of the bis(benzoxazinyl)phthalimidine and a curing product of the optional epoxy compound. Within this range, the filler amount can be 10 to 500 weight parts, or 20 to 400 weight parts.

The invention includes at least the following embodiments.

Aspect 1: A bis(benzoxazinyl)phthalimidine having the structure

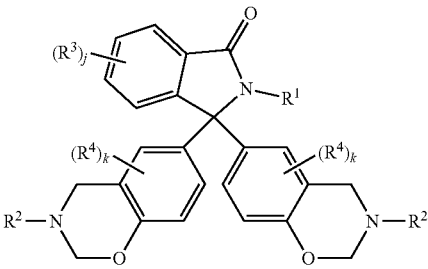

wherein $R^1$ is hydrogen, $C_1$-$C_6$ alkyl, phenyl, or phenyl substituted with up to five substituents independently selected from halogen and $C_1$-$C_6$ alkyl; each occurrence of $R^2$ is independently selected from the group consisting of unsubstituted or substituted $C_1$-$C_{30}$ hydrocarbyl; each occurrence of $R^3$ is independently $C_1$-$C_6$ alkyl; j is 0, 1, 2, 3, or 4; each occurrence of $R^4$ is independently selected from the group consisting of $C_1$-$C_{12}$ alkyl, $C_2$-$C_{12}$ alkenyl, and $C_1$-$C_{12}$ alkoxyl; and each occurrence of k is independently 0, 1, 2, or 3.

Aspect 2: The bis(benzoxazinyl)phthalimidine of aspect 1, wherein $R^1$ is phenyl, or phenyl substituted with 1, 2, 3, 4, or 5 substituents independently selected from halogen and $C_1$-$C_6$ alkyl.

Aspect 3: The bis(benzoxazinyl)phthalimidine of aspect 1, wherein $R^1$ is phenyl.

Aspect 4: The bis(benzoxazinyl)phthalimidine of any one of aspects 1-3, wherein each occurrence of $R^2$ is independently selected from the group consisting of $C_1$-$C_{12}$ alkyl (including, for example, cyclopropyl, cyclobutyl, cyclopentyl, cyclohexyl, cycloheptyl, and cyclooctyl), anthracenyl, biphenyl, cyclohexenyl, cyclopentenyl, indanyl, naphthyl, and phenyl.

Aspect 5: The bis(benzoxazinyl)phthalimidine of any one of aspects 1-3, wherein each occurrence of $R^2$ is $C_1$-$C_{12}$ alkyl or phenyl.

Aspect 6: The bis(benzoxazinyl)phthalimidine of any one of aspects 1-5, wherein j is 0, and each occurrence of k is 0.

Aspect 7: The bis(benzoxazinyl)phthalimidine of aspect 1, wherein $R^1$ is phenyl, each occurrence of $R^2$ is phenyl, j is 0, and each occurrence of k is 0.

Aspect 8: A curable composition comprising the bis (benzoxazinyl)phthalimidine of any one of aspects 1-7.

Aspect 9: The curable composition of aspect 8, further comprising an epoxy resin selected from the group consisting of aliphatic epoxy resins, cycloaliphatic epoxy resins, aromatic epoxy resins, dicyclopentadiene-type (DCPD-type) epoxy resins, and combinations thereof.

Aspect 10: The curable composition of aspect 9, wherein the epoxy resin is selected from the group consisting of bisphenol-A diglycidyl ether, bisphenol-F diglycidyl ether, neopentylglycol diglycidyl ether, 3,4-epoxycyclohexylmethyl-3,4-epoxycyclohexane carboxylate, N,N-diglycidyl-4-glycidyloxyaniline, N,N',N'-tetraglycidyl-4,4'-diaminodiphenylmethane, 2-phenyl-3,3-bis(4-glycidyloxyphenyl) phthalimidine, and combinations thereof.

Aspect 11: The curable composition of aspect 9, wherein the epoxy resin is a diglycidyl ether compound having the structure

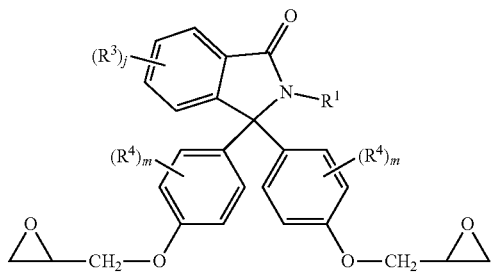

wherein R' is hydrogen, $C_1$-$C_6$ alkyl, phenyl, or phenyl substituted with up to five substituents independently selected from halogen and $C_1$-$C_6$ alkyl; each occurrence of $R^3$ is independently $C_1$-$C_6$ alkyl; j is 0, 1, 2, 3, or 4; each occurrence of $R^4$ is independently selected from the group consisting of $C_1$-$C_{12}$ alkyl, $C_2$-$C_{12}$ alkenyl, and $C_1$-$C_{12}$ alkoxyl; and each occurrence of m is independently 0, 1, 2, 3, or 4.

Aspect 12: The curable composition of any one of aspects 7-10, comprising the bis(benzoxazinyl)phthalimidine of aspect 7.

Aspect 13: A composite comprising a reinforcing filler and a curing product of the bis(benzoxazinyl)phthalimidine of any one of aspects 1-7.

Aspect 14: The composite of aspect 13, comprising a reinforcing filler and a curing product of the bis(benzoxazinyl)phthalimidine of aspect 7.

All ranges disclosed herein are inclusive of the endpoints, and the endpoints are independently combinable with each other. Each range disclosed herein constitutes a disclosure of any point or sub-range lying within the disclosed range.

The invention is further illustrated by the following non-limiting examples.

EXAMPLES

Synthesis of 2-Phenyl-3,3-bis(3-phenyl-3,4-dihydro-2H-benzo [e][1,3]oxazin-6-yl)isoindolin-1-one (PPPBP-BZ). The FIGURE is a chemical scheme for the synthesis. 2-Phenyl-3,3-bis(4-hydroxyphenyl)phthalimidine (PPPBP, 25 grams, 0.0636 mole) was added to a 500 milliliter 3-neck flask equipped with a Dean-Stark apparatus and a condenser. The PPPBP was allowed to partially dissolve in 45 milliliters of toluene at 80° C. for about 30 minutes. To this mixture, paraformaldehyde (12.4 grams, 0.4 mole) was added followed by aniline (13 milliliters, 0.1424 mole) and 15 milliliters of ethanol. The reaction mixture was allowed to stir for 24 hours at 85 to 90° C. The solution was allowed to cool to room temperature and the solvent was removed under reduced pressure to yield an oil. The oil was dispersed in a small amount of methylene chloride and precipitated into hexane to yield a white powder (crude yield 33 grams, 82.64%). The crude product was purified using a silica plug (solvent: hexane+ethyl acetate), where PPPBP-BZ was retained in the silica gel. The pure product was obtained by washing the silica gel with chloroform and filtering out the silica gel. The filtrate was then precipitated in hexane and dried. A proton nuclear magnetic resonance ($^1$H NMR) spectrum confirmed the formation of pure PPPBP-BZ as the product. The 1H NMR spectrum was obtained using a Mercury Plus 400 Megahertz $^1$H-NMR spectrometer.

Synthesis of 3,3-bis(3-phenyl-3,4-dihydro-2H-benzo [e] [1,3]oxazin-6-yl)isobenzofuran-1(3H)-one (Phen-BZ, Phenolphthalein bis(benzoxazine)). The synthesis of phenolphthalein bis(benzoxazine) was performed according to literature reports. See, P. Yang and Y. Gu, Journal of Polymer Research, 2011, volume 18, pages 1725-1733; P. Yang, X. Wang, and Y. Gu, Journal of Polymer Research, 2012, volume 19, page 9901; and R. Tietz, D. Orser, Y. Blyakhman, M. Bryant, and B.-S. Lin, "Benzoxazine Compounds Derived from Phenolphthalein Having Flame-Retardant Properties and a Process for Their Preparation," European Patent No., EP 1 797 081 B1, 2005. Phenolphthalein (19.91 grams, 0.0626 mole) was added to a 500 milliliter 3-neck flask equipped with a Dean-Stark apparatus and a condenser. The phenolphthalein was allowed to partially dissolve in 45 milliliters toluene at 80° C. for about 30 minutes. To this solution, paraformaldehyde (12.4 grams, 0.4 mole) was added, followed by aniline (13 milliliters, 0.14 moles) and 15 milliliters of ethanol. The reaction was allowed to stir for 24 hours at 85 to 90° C. The solution was allowed to cool to room temperature and the solvent was removed under reduced pressure to yield an oil. The oil was dispersed in small amount of methylene chloride and precipitated into hexane to yield yellow powder (crude yield 39 grams, 114.7%). The crude product was purified using preparatory HPLC in hexane and ethyl acetate solvent. The pure fractions were mixed and concentrated in vacuum to yield a colorless oil which was mixed with methylene chloride and precipitated into hexane to yield a pale off-white solid. $^1$H NMR spectrum confirmed the formation of pure Phen-BZ as the product.

Cured thermosets were prepared by the following method. A small amount of the solid (~60 mg) in an aluminum pan was placed in a Blue M Oven from Thermal Product Solutions and cured at atmospheric pressure according to the curing protocol detailed below in Table 1.

TABLE 1

| Step No. | Temperature (° C.) | Equilibration Time (min) |
| --- | --- | --- |
| 1 | 140 | 60 |
| 2 | 160 | 60 |
| 3 | 180 | 60 |

TABLE 1-continued

| Step No. | Temperature (° C.) | Equilibration Time (min) |
|---|---|---|
| 4 | 200 | 30 |
| 5 | 220 | 30 |

Differential Scanning Calorimetry (DSC) according to ASTM D3418-15 was used to determine the melting temperatures ($T_m$) of the bis(benzoxazine) compounds, and the glass transition temperatures ($T_g$) of the cured products of the bis(benzoxazine) compounds. Testing was performed using a Q1000 differential scanning calorimeter from TA Instruments. In a typical procedure, a polymer sample (10-20 milligrams) was heated from 40° C. to 325° C. at 20° C./minute, held at 325° C. for 1 minute, cooled back to 40° C. at 20° C./minute, then held at 40° C. for 1 minute. $T_m$ values for the bis(benzoxazine) compounds were determined based on the heating portion of this first thermal cycle, and curing occurred in the high temperature portion of the cycle. A second thermal cycle was conducted under the same conditions, and the heating portion of this second thermal cycle was used to determine $T_g$ values for the cured products of the bis(benzoxazine) compounds.

Thermal Gravimetric Analysis (TGA) was performed with a TA Q800 TGA. The samples were scanned from 40° C. to 800° C. under nitrogen and air with a heating rate of 20° C./minute. This analysis was also used to determine the temperature of peak decomposition (also referred as the onset decomposition temperature), and the char yield at the end of the TGA run.

The property results in Table 2 show that the bis(benzoxazinyl)phthalimidine exhibits a substantially higher melting temperature and a substantially higher exotherm onset temperature relative to the corresponding bis(benzoxazinyl) phenophthalein.

TABLE 2

| | | PPPBP-BZ | Phen-BZ |
|---|---|---|---|
| Melting temperature (° C.) | | 139.5 | ~95 |
| Onset of Exotherm (° C.) | | ~210 | ~190 |
| $T_g$ of cured material (° C.) | | 238 | 235 |
| Onset of decomposition (° C.) | $N_2$ | 349 | 320 |
| | air | 383 | 300 |
| 1% weight loss (° C.) | $N_2$ | 203 | 276 |
| | air | 76 | 267 |
| 5% weight loss (° C.) | $N_2$ | 350 | 357 |
| | air | 369 | 381 |
| Char yield (%) | $N_2$ | 44.97 | 59.45 |
| | air | 0.89 | 0 |

The invention claimed is:

1. A bis(benzoxazinyl)phthalimidine having the structure

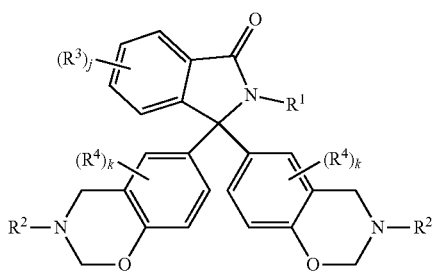

wherein
$R^1$ is hydrogen, $C_1$-$C_6$ alkyl, phenyl, or phenyl substituted with up to five substituents independently selected from halogen and $C_1$-$C_6$ alkyl;
each occurrence of $R^2$ is independently selected from the group consisting of unsubstituted or substituted $C_1$-$C_{30}$ hydrocarbyl;
each occurrence of $R^3$ is independently $C_1$-$C_6$ alkyl;
j is 0, 1, 2, 3, or 4;
each occurrence of $R^4$ is independently selected from the group consisting of $C_1$-$C_{12}$ alkyl, $C_2$-$C_{12}$ alkenyl, and $C_1$-$C_{12}$ alkoxyl; and
each occurrence of k is independently 0, 1, 2, or 3.

2. The bis(benzoxazinyl)phthalimidine of claim 1, wherein $R^1$ is phenyl, or phenyl substituted with 1, 2, 3, 4, or 5 substituents independently selected from halogen and $C_1$-$C_6$ alkyl.

3. The bis(benzoxazinyl)phthalimidine of claim 1, wherein $R^1$ is phenyl.

4. The bis(benzoxazinyl)phthalimidine of claim 1, wherein each occurrence of $R^2$ is independently selected from the group consisting of $C_1$-$C_{12}$ alkyl, anthracenyl, biphenyl, cyclohexenyl, cyclopentenyl, indanyl, naphthyl, and phenyl.

5. The bis(benzoxazinyl)phthalimidine of claim 1, wherein each occurrence of $R^2$ is $C_1$-$C_{12}$ alkyl or phenyl.

6. The bis(benzoxazinyl)phthalimidine of claim 1, wherein j is 0, and each occurrence of k is 0.

7. The bis(benzoxazinyl)phthalimidine of claim 1, wherein $R^1$ is phenyl, each occurrence of $R^2$ is phenyl, j is 0, and each occurrence of k is 0.

8. A curable composition comprising the bis(benzoxazinyl)phthalimidine of claim 1.

9. The curable composition of claim 8, further comprising an epoxy resin selected from the group consisting of aliphatic epoxy resins, cycloaliphatic epoxy resins, aromatic epoxy resins, dicyclopentadiene-type (DCPD-type) epoxy resins, and combinations thereof.

10. The curable composition of claim 9, wherein the epoxy resin is selected from the group consisting of bisphenol-A diglycidyl ether, bisphenol-F diglycidyl ether, neopentylglycol diglycidyl ether, 3,4-epoxycyclohexylmethyl-3,4-epoxycyclohexane carboxylate, N,N-diglycidyl-4-glycidyloxyaniline, N,N,N',N'-tetraglycidyl-4,4'-diaminodiphenylmethane, 2-phenyl-3,3-bis(4-glycidyloxyphenyl)phthalimidine, and combinations thereof.

11. The curable composition of claim 9, wherein the epoxy resin is a diglycidyl ether compound having the structure

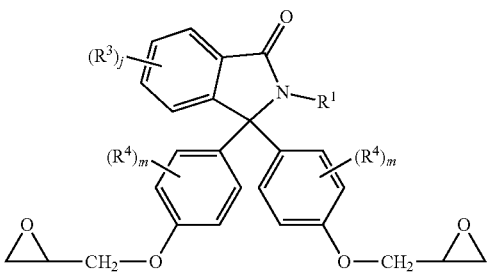

wherein
- $R^1$ is hydrogen, $C_1$-$C_6$ alkyl, phenyl, or phenyl substituted with up to five substituents independently selected from halogen and $C_1$-$C_6$ alkyl;
- each occurrence of $R^3$ is independently $C_1$-$C_6$ alkyl;
- j is 0, 1, 2, 3, or 4;
- each occurrence of $R^4$ is independently selected from the group consisting of $C_1$-$C_{12}$ alkyl, $C_2$-$C_{12}$ alkenyl, and $C_1$-$C_{12}$ alkoxyl; and
- each occurrence of m is independently 0, 1, 2, 3, or 4.

12. The curable composition of claim 7, comprising the bis(benzoxazinyl)phthalimidine of claim 7.

13. A composite comprising a reinforcing filler and a curing product of the bis(benzoxazinyl)phthalimidine of claim 1.

14. The composite of claim 13, comprising a reinforcing filler and a curing product of the bis(benzoxazinyl)phthalimidine of claim 7.

\* \* \* \* \*